US008027729B2

(12) United States Patent  
Sunagawa et al.

(10) Patent No.: US 8,027,729 B2  
(45) Date of Patent: Sep. 27, 2011

(54) MICRO INTEGRATED CARDIAC PACEMAKER AND DISTRIBUTED CARDIAC PACING SYSTEM

(75) Inventors: Kenji Sunagawa, Fukuoka (JP); Masaru Sugimachi, Osaka (JP); Masashi Inagaki, Chiba (JP)

(73) Assignees: National Cerebral and Cardiovascular Center, Osaka (JP); Fujikin Corporated, Osaka (JP)

( * ) Notice: Subject to any disclaimer, the term of this patent is extended or adjusted under 35 U.S.C. 154(b) by 879 days.

(21) Appl. No.: 10/523,538

(22) PCT Filed: Aug. 4, 2003

(86) PCT No.: PCT/JP03/09886  
§ 371 (c)(1),  
(2), (4) Date: Feb. 3, 2005

(87) PCT Pub. No.: WO2004/012811  
PCT Pub. Date: Feb. 12, 2004

(65) Prior Publication Data  
US 2005/0288717 A1    Dec. 29, 2005

(30) Foreign Application Priority Data  
Aug. 5, 2002   (JP) .............. PCT/JP02/07972

(51) Int. Cl.  
*A61N 1/375* (2006.01)

(52) U.S. Cl. ............................ 607/36; 607/35

(58) Field of Classification Search ............... 607/35, 607/36  
See application file for complete search history.

(56) References Cited

U.S. PATENT DOCUMENTS

| 3,861,397 | A |   | 1/1975  | Rao et al. ............... 128/419 |
| 3,943,936 | A | * | 3/1976  | Rasor et al. ............. 607/35  |
| 5,270,128 | A | * | 12/1993 | Reichert et al. .......... 429/29  |
| 5,411,535 | A | * | 5/1995  | Fujii et al. ............. 607/32  |
| 6,294,281 | B1 | * | 9/2001 | Heller ................... 429/43  |

FOREIGN PATENT DOCUMENTS

| JP | 49-108538  | 10/1974 |
| JP | S49-108538 | 10/1974 |
| JP | 05-245215  | 9/1993  |

* cited by examiner

Primary Examiner — Michael Kahelin  
(74) Attorney, Agent, or Firm — Brown & Michaels, PC

(57) ABSTRACT

A micro integrated cardiac pacemaker includes a control unit for outputting a control signal according to cardiograph information, heart stimulating means for stimulating heart tissue in response to the control signal, cardiograph information extracting means for extracting cardiograph information and outputting it to the control unit, and a power supply unit for supplying drive power. The power supply unit is a biological fuel cell that takes out electrons by oxidation of a biological fuel. The biological fuel cell includes an anode and a cathode. An oxidase of a biological fuel and a mediator are immobilized on the cathode. Blood and/or body fluid are used as an electrolytic solution, and a biological fuel and oxygen in the blood and/or the fluid are used. The biological fuel cell is attached to the end of a catheter and implanted into the heart, and the catheter is withdrawn, without incising the breast.

7 Claims, 10 Drawing Sheets

MICRO INTEGRATED CARDIAC PACEMAKER AND DISTRIBUTED CARDIAC PACING SYSTEM

BACKGROUND OF THE INVENTION

1. Field of the Invention

The present invention concerns an ultra miniature integrated cardiac pacemaker and distributed cardiac pacing system. The invention provides an ultra miniature integrated cardiac pacemaker and distributed cardiac pacing system that allows pacing of the heart without the need for conventional lead wires that connect the electrodes and the main body of the pacemaker, and allows implantation by catheter manipulation without incising the chest wall, which avoids imposing an extra burden on the user.

In this invention, "ultra miniature" refers to the minute size of the pacemaker to the extent that it can be attached to the tip of a catheter.

2. Description of Related Art

A cardiac pacemaker is a device that controls the rhythm of the heart by delivering electrical impulses to the heart, and is indicated for use in patients with symptoms of bradyarrhythmia.

A conventional cardiac pacemaker includes the main body of the cardiac pacemaker (generator), lead wires, and electrodes that transmit a stimulating pulse to the myocardium. The main body of the cardiac pacemaker and the electrodes are connected by lead wires. However, conventional pacemakers have the following problems.

Since the main body of the cardiac pacemaker and the electrodes are connected by lead wires, cases of breaking of the lead wires have occurred. Breakage of the lead wires results in defective pacing. In addition, there have been also cases of venous obstruction by the lead wires.

Moreover, during the early stages after implantation of the cardiac pacemaker, a shift in position of the electrodes may cause defective pacing. When a shift in position of the electrodes occurs, a second operation has to be performed, which adds extra strain for the patient.

Furthermore, if there is a defective hermetic sealing structure at the junction between the cardiac pacemaker main body and the lead wires, this may lead to defective pacemaker movement. Problems with electrical safety have also occurred.

In the Unexamined Japanese Patent Publication Heisei No. 5-245215, a cardiac pacemaker is described in which the signals for cardiac stimulation are delivered from the cardiac pacemaker main body to the stimulation electrodes by wireless transmission, thus eliminating the lead wires between the cardiac pacemaker main body and the electrodes.

However, even for this type of cardiac pacemaker, surgical implantation of the pacemaker cannot be avoided, and there have been cases in which skin necrosis occurred at the cardiac pacemaker implantation site.

Also, in the above-mentioned cardiac pacemaker, although wireless communication is conducted between the pacemaker main body and the electrodes, there is no communication between the electrodes. Synchrony between the multiple electrodes being used is controlled by the pacemaker main body.

The present invention was developed in order to solve the above problems, and to provide an ultra miniature integrated cardiac pacemaker and distributed cardiac pacing system with the following features: the generator function of electric stimulus by the pacemaker main body is integrated with the electrodes, thus allowing pacing of the heart without the need for conventional lead wires connecting the electrodes and pacemaker main body. By integrating the control unit of the pacemaker main body and the electrodes, there is no need to implant the pacemaker main body, which avoids imposing an extra burden on the user.

SUMMARY OF THE INVENTION

The ultra miniature integrated cardiac pacemaker of the present invention requires no chest incision, and is implanted in the heart by attaching it to the tip of a catheter and extracting the catheter after implanting.

In one embodiment, the pacemaker includes a control unit that outputs control signals, a heart stimulating means that responds to the control signal and electrically stimulates the heart tissue, an electrocardiographic information detecting means that detects the electrocardiographic information and outputs it to the control unit, and a power unit that supplies the driving power.

The control unit outputs the control signals based on electrocardiographic information.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

In another embodiment of the present invention, an ultra miniature integrated cardiac pacemaker includes a control unit that outputs control signals, a heart stimulating means that responds to the control signal and electrically stimulates the heart tissue, an electrocardiographic information detecting means that detects the electrocardiographic information and outputs it to the control unit, a transmitting means that modulates the electrocardiographic information and control signals to be sent outside, and a power unit that supplies the driving power.

The control unit outputs the control signals based on electrocardiographic information.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

In a third embodiment, an ultra miniature integrated cardiac pacemaker includes a control unit that outputs control signals, a heart stimulating means that responds to the control signal and electrically stimulates the heart tissue, an electrocardiographic information detecting means that detects the electrocardiographic information and outputs it to the control unit, a receiving means that receives and demodulates the information sent from outside, and a power unit that supplies the driving power. It is designed such that the information sent from outside is input into the control unit.

The control unit outputs control signals based on information sent from outside and/or electrocardiographic information.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

In yet another embodiment, an ultra miniature integrated cardiac pacemaker includes a control unit that outputs control signals, a heart stimulating means that responds to the control signal and electrically stimulates the heart tissue, an electrocardiographic information detecting means that detects the electrocardiographic information and outputs it to the control unit, a transmitting means that modulates the electrocardiographic information and control signals to be sent outside, a receiving means that receives and demodulates the information sent from outside, and a power unit that supplies the driving current. It is designed such that the information sent from outside is input into the control unit.

The control unit outputs control signals based on information sent from outside and/or electrocardiographic information.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as electrolyte solution and utilizes biological fuels and oxygen in blood and/or body fluid.

Another embodiment discloses a cardiac pacing system including an ultra miniature integrated cardiac pacemaker placed in the atrial myocardium.

The ultra miniature integrated cardiac pacemaker is equipped with a control unit that outputs control signals, a power unit that supplies the driving power, a heart stimulating means that responds to the control signals and electrically stimulates the atrial myocardium, and an electrocardiographic information detecting means that detects the electrocardiographic information including at least intracardiac P wave information.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

The control unit is equipped with a stimulation timing determining means that decides the timing of stimulation to generate control signals, and a stimulation timing changing means that changes the timing of stimulation to generate control signals. It is characterized by the ability to change the timing of stimulation to generate the control signal, in case intracardiac P wave information is detected within a preset time interval.

Yet another embodiment concerns a distributed cardiac pacing system including an electrocardiographic information detecting device placed in the atrial myocardium and an ultra miniature integrated cardiac pacemaker placed in the ventricular myocardium.

The electrocardiographic information detecting device is equipped with an electrocardiographic information detecting means that detects the electrocardiographic information including at least intracardiac P wave information, a transmitting means that modulates the electrocardiographic information detected and sends the information to the ultra miniature integrated cardiac pacemaker, and a power unit that supplies the driving current.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

The ultra miniature integrated cardiac pacemaker is equipped with a receiving means that receives and demodulates the electrocardiographic information sent from the electrocardiographic information detection device, a control unit that outputs control signals, a power unit that supplies the driving power, and a heart stimulating means that responds to the control signal and electrically stimulates the ventricular myocardium.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

The control unit is equipped with a stimulation timing determining means that decides the timing of stimulation to generate the control signals, and a stimulation timing changing means that changes the timing of stimulation to generate the control signals.

It is characterized by a mechanism to generate control signals when intracardiac QRS complex information is not detected within a given time after the detection of intracardiac P wave, and suppress the control signals when QRS complex information is detected within a given time after the detection of intracardiac P wave information.

Another embodiment discloses a distributed cardiac pacing system including a first ultra miniature integrated cardiac pacemaker placed in the atrial myocardium and a second ultra miniature integrated cardiac pacemaker placed in the ventricular myocardium.

The first ultra miniature integrated cardiac pacemaker is equipped with a control unit that outputs control signals, a power unit that supplies the driving power, a heart stimulating means that responds to the control signal and electrically stimulates the atrial myocardium, an electrocardiographic information detecting means that detects the electrocardiographic information including at least intracardiac P wave information, a transmitting means that modulates the electrocardiographic information and sends the information to the second ultra miniature integrated cardiac pacemaker, and a receiving means that receives and demodulates the electrocardiographic information sent from the second ultra miniature integrated cardiac pacemaker.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

The electrocardiographic information sent from the second ultra miniature integrated cardiac pacemaker is input into the control unit; and the control unit is equipped with a stimulation timing determining means that decides the timing of stimulation to generate the control signals, and a stimulation timing changing means that changes the timing of stimulation to generate the control signals.

The second ultra miniature integrated cardiac pacemaker is equipped with a control unit that outputs control signals, a power unit that supplies the driving power, a heart stimulating means that responds to the control signal and electrically stimulates the ventricular myocardium, an electrocardiographic information detecting means that detects the electrocardiographic information including at least intracardiac QRS complex information, a transmitting means that modulates the electrocardiographic information and sends the information to the first ultra miniature integrated cardiac pacemaker, and a receiving means that receives and demodulates the electrocardiographic information sent by the first ultra miniature integrated cardiac pacemaker.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as electrolyte solution and utilizes biological fuels and oxygen in blood and/or body fluid.

The electrocardiographic information sent from the first ultra miniature integrated cardiac pacemaker is input into the control unit; and the control unit is equipped with a stimulation timing determining means that decides the timing of stimulation to generate the control signal, and a stimulation timing changing means that changes the timing of stimulation to generate the control signal.

The control unit of the first ultra miniature integrated cardiac pacemaker generates the control signal when intracardiac P wave information is not detected within a given time interval, and suppresses the generation of control signals when intracardiac P wave information is detected within a given time.

The control unit of the second ultra miniature integrated cardiac pacemaker generates control signals when intracardiac QRS complex information is not detected within a given time after detection of intracardiac P wave information, and suppresses the generation of control signals when intracardiac QRS complex information is detected within a given time after detection of intracardiac P wave information.

The system is also characterized by the following mechanism: if the second ultra miniature integrated cardiac pacemaker detects intracardiac QRS complex information due to spontaneous ventricular contraction, the control unit of the first ultra miniature integrated cardiac pacemaker suppresses the detection of intracardiac P wave information for a given time interval.

Another embodiment discloses a distributed cardiac pacing system including an electrocardiographic information detection device placed in the atrial myocardium and multiple ultra miniature integrated cardiac pacemakers placed in the ventricular myocardium.

The electrocardiographic information detection device is equipped with an electrocardiographic information detecting means that detects the electrocardiographic information including at least intracardiac P wave information, a transmitting means that modulates the detected electrocardiographic information and sends the information to the ultra miniature integrated cardiac pacemakers, and a power unit that supplies the driving power.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as electrolyte solution and utilizes biological fuels and oxygen in blood and/or body fluid.

The ultra miniature integrated cardiac pacemakers are equipped with a control unit that outputs control signals, a power unit that supplies the driving power, a heart stimulating means that responds to the control signals and electrically stimulates the ventricular muscle, an electrocardiographic information detecting means that detects the electrocardiographic information including at least intracardiac QRS complex information, a transmitting means that modulates the electrocardiographic information and sends the information to other ultra miniature integrated cardiac pacemakers, and a receiving means that receives and demodulates the electrocardiographic information sent from other ultra miniature integrated cardiac pacemakers.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

The electrocardiographic information sent from other ultra miniature integrated cardiac pacemakers is input into the control unit; and the control unit is equipped with a stimulation timing determining means that decides the timing of stimulation to generate the control signals, and a stimulation timing changing means that changes the timing of stimulation to generate the control signals.

The system is characterized by the following mechanism: when individual ultra miniature integrated cardiac pacemakers do not detect intracardiac QRS complex information within the respective preset times after detection of intracardiac P wave information, the control units of the ultra miniature integrated cardiac pacemakers generate control signals; whereas when QRS complex information is detected within given time intervals after detection of intracardiac P wave information, the control units generate control signals synchronous to the earliest timing at which the intracardiac QRS complex information is first detected.

Yet another embodiment discloses a distributed cardiac pacing system including a first ultra miniature integrated cardiac pacemaker placed in the atrial myocardium and multiple second ultra miniature integrated cardiac pacemakers placed in the ventricular myocardium.

The first ultra miniature integrated cardiac pacemaker is equipped with a control unit that outputs control signals, a power unit that supplies the driving power, a heart stimulating means that responds to the control signals and electrically stimulates the atrial myocardium, an electrocardiographic information detecting means that detects the electrocardiographic information including at least intracardiac P wave information, a transmitting means that modulates the electrocardiographic information and sends the information to multiple second ultra miniature cardiac pacemakers, and a receiving means that receives and demodulates the electrocardiographic information sent by the multiple second ultra miniature integrated cardiac pacemakers.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as electrolyte solution and utilizes biological fuels and oxygen in blood and/or body fluid.

The electrocardiographic information sent from the multiple second ultra miniature integrated cardiac pacemakers are input into the control unit; and the control unit is equipped with a stimulation timing determining means that decides the timing of stimulation to generate the control signals, and a stimulation timing changing means that changes the timing of stimulation to generate the control signals.

The multiple second ultra miniature integrated cardiac pacemakers are each equipped with a control unit that outputs control signals, a power unit that supplies the driving current, a heart stimulating means that responds to the control signal and electrically stimulates the ventricular myocardium, an electrocardiographic information detecting means that detects the electrocardiographic information including at least intracardiac QRS complexes, a transmitting means that modulates the electrocardiographic information and sends the information to the first and other second ultra miniature cardiac pacemakers, and a receiving means that receives and demodulates the electrocardiographic information sent from the first and other second ultra miniature integrated cardiac pacemakers.

The power unit is preferably a biological fuel cell that extracts electrons from oxidative reactions of biological fuels. The biological fuel cell is composed of an anode electrode and a cathode electrode. The anode electrode is coated with immobilized oxidative enzymes for biological fuels and mediators. The biological fuel cell uses blood and/or body fluid as an electrolyte solution and utilizes biological fuels and oxygen in blood and/or body fluid.

The electrocardiographic information sent from the first and other second ultra miniature integrated cardiac pacemakers is input into the control unit; and the control unit is equipped with a stimulation timing determining means that decides the timing of stimulation to generate the control signals, and a stimulation timing changing means that changes the timing of stimulation to generate the control signals.

The control unit of the first ultra miniature integrated cardiac pacemaker generates control signals when intracardiac P wave information is not detected within a given time interval, and suppresses the generation of control signal when intracardiac P wave information is detected within a given time.

The control units of the second ultra miniature integrated cardiac pacemakers generate control signals when intracardiac QRS complex information is not detected by individual ultra miniature integrated cardiac pacemakers within the respective preset time intervals after the detection of intracardiac P wave information; whereas if intracardiac QRS complex information is detected within the given time intervals after the detection of intracardiac P wave information, the control units generate control signals synchronous to the earliest timing at which intracardiac QRS complex information is detected.

The system is also characterized by the following mechanism: when one of the multiple second ultra miniature integrated cardiac pacemakers detects intracardiac QRS complex information due to spontaneous ventricular contraction, the control unit of the first ultra miniature integrated cardiac pacemaker suppresses the detection of intracardiac P wave information for a given interval.

DETAILED DESCRIPTION OF THE INVENTION

Figure 1:
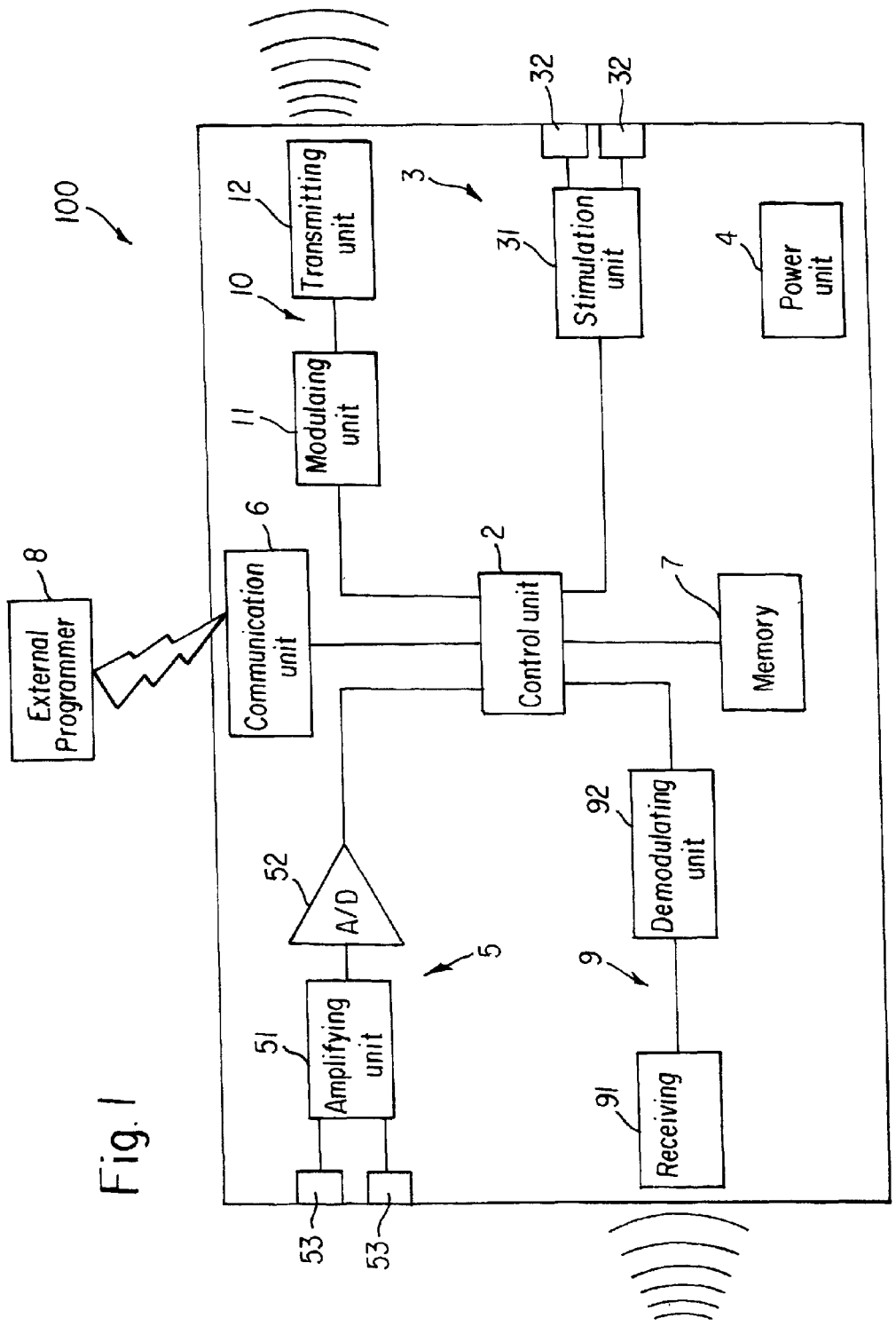
FIG. 1 is a simplified block diagram of an ultra miniature integrated cardiac pacemaker in accordance with the first embodiment.

The present invention is described in detail below while referring to the figures. FIG. 1 is a simplified block diagram of an ultra miniature integrated cardiac pacemaker (100) in accordance with a first embodiment of this invention.

The ultra miniature integrated cardiac pacemaker (100) in this embodiment is composed of a control unit (2) that outputs control signals, a heart stimulating means (3) that responds to the control signals and electrically stimulates the heart tissue, an electrocardiographic information detecting means (5) that detects the electrocardiographic information and outputs it to the control unit (2), a transmitting means (10) that modulates the control signals output from the control unit (2) and/or electrocardiographic information detected by the electrocardiographic information detecting means (5) and sends the information outside, a receiving means (9) that receives and demodulates the information sent from outside, and a power unit (4) that supplies the driving current.

The heart stimulating means (3) responds to the control signal output from the control unit (2) and electrically stimulates the heart tissue. The heart stimulating means (3) as shown in the diagram is able to stimulate the heart tissue. The heart stimulating means (3) includes a stimulating unit (31) that responds to the control signals output from the control unit (2) and outputs heart stimulating pulses to stimulate the heart tissue, and two heart stimulating electrodes (32) that stimulate the heart tissue in response to the output pulses.

The electrocardiographic information detecting means (5) detects the electrocardiographic information at the site where the ultra miniature integrated cardiac pacemaker is placed. The detected electrocardiographic information is output to the control unit (2). The electrocardiographic information detected by the electrocardiographic information detecting means (5) includes P wave information, QRS complex information, T wave information, or Q-T time, A-H time, H-V time (where A is atrial potential, H is His bundle potential, and V is ventricular potential).

The electrocardiographic information detecting means (5) as shown in the diagram is composed of two electrocardiographic information recording electrodes (53) that detect the applied site electrocardiographic information at the placement site, an amplifying unit (51) that amplifies the electrocardiogram, and an A/D conversion (52) unit that converts the detected electrocardiographic information into digital signals. The electrocardiographic information detecting means (5) is designed such that the converted electrocardiographic information is output to the control unit (2).

The transmitting means (10) is composed of a modulating unit (11) that inputs and modulates the control signals output from the control unit (2) and/or electrocardiographic information, and a transmitting unit (12) that sends the modulated control signals to the outside via carrier waves; by which the modulated control signals are sent to the outside (such as to other ultra miniature integrated cardiac pacemakers, not shown in the diagram).

By transmitting control signals and electrocardiographic information via carrier waves to outside sites such as other cardiac pacemakers, it is possible, for example, to activate two or more cardiac pacemakers synchronously. Moreover, since carrier waves are used for transmission, there is no need for lead wires, and this method avoids imposing an extra burden on the user.

The receiving means (9) is composed of a receiving unit (91) that receives information transmitted from the outside via carrier waves, and a demodulating unit (92) that demodulates the information received. It is designed such that the demodulated information is input into the control unit (2). Based on this information and/or electrocardiographic information, control signals are generated in the control unit (2) and output to the heart stimulating means (3).

The information transmitted from the outside includes electrocardiographic information and control signals sent from other cardiac pacemakers.

By equipping the receiving means (9) that receives information from, for instance, other cardiac pacemakers, it is possible to activate the cardiac pacemaker synchronously with other cardiac pacemakers. Moreover, since there is no need for lead wires, this method avoids imposing extra burden on the user.

Possible modes of communication between pacemakers executed by the transmitting means (10) and receiving means (9) include, but are not limited to, spread spectrum communication using radio waves or ultrasound waves, and ultra wide band communication. There is no restriction on the mode of communication. Any method can be used as long as it provides reliable communication between pacemakers.

The power unit (4) is designed to supply a power source necessary to drive the ultra miniature integrated cardiac pacemaker. As a power unit (4), in general, it is possible to use a lithium battery or fuel cells. However, in the conventional cardiac pacemakers, the power unit that supplies the electrical source is the largest component. To ultra-miniaturize the cardiac pacemaker, it is necessary to miniaturize the power unit. For the ultra miniature integrated cardiac pacemaker (100) according to the present invention, a biological fuel cell is preferably used as the power unit (4).

If a biological fuel cell is used as the power unit, biological fuels such as glucose and oxygen, which are necessary to drive the biological fuel cell, are available in constant supply inside the body. The volume of the power unit (4) depends only on the size of the electrodes, making it possible to miniaturize the volume of the power unit (4). Moreover, metabolites and intermediate metabolic products of sugars (e.g., glucose), such as water, carbon dioxide and gluconolactone, are safe for the human body and they are rapidly removed from the vicinity of the electrodes by blood flow. Biological fuel cells that use enzymes as catalysts can operate under mild conditions such as neutral pH and room temperature.

One example of a biological fuel cell used in this invention is the well-known conventional biological fuel cell that extracts electrons from oxidative reactions of biological fuels. This biological fuel cell uses sugars (such as glucose) and oxygen, both supplied by the body, as fuels, and utilizes enzymes as biological catalysts.

Figure 2:
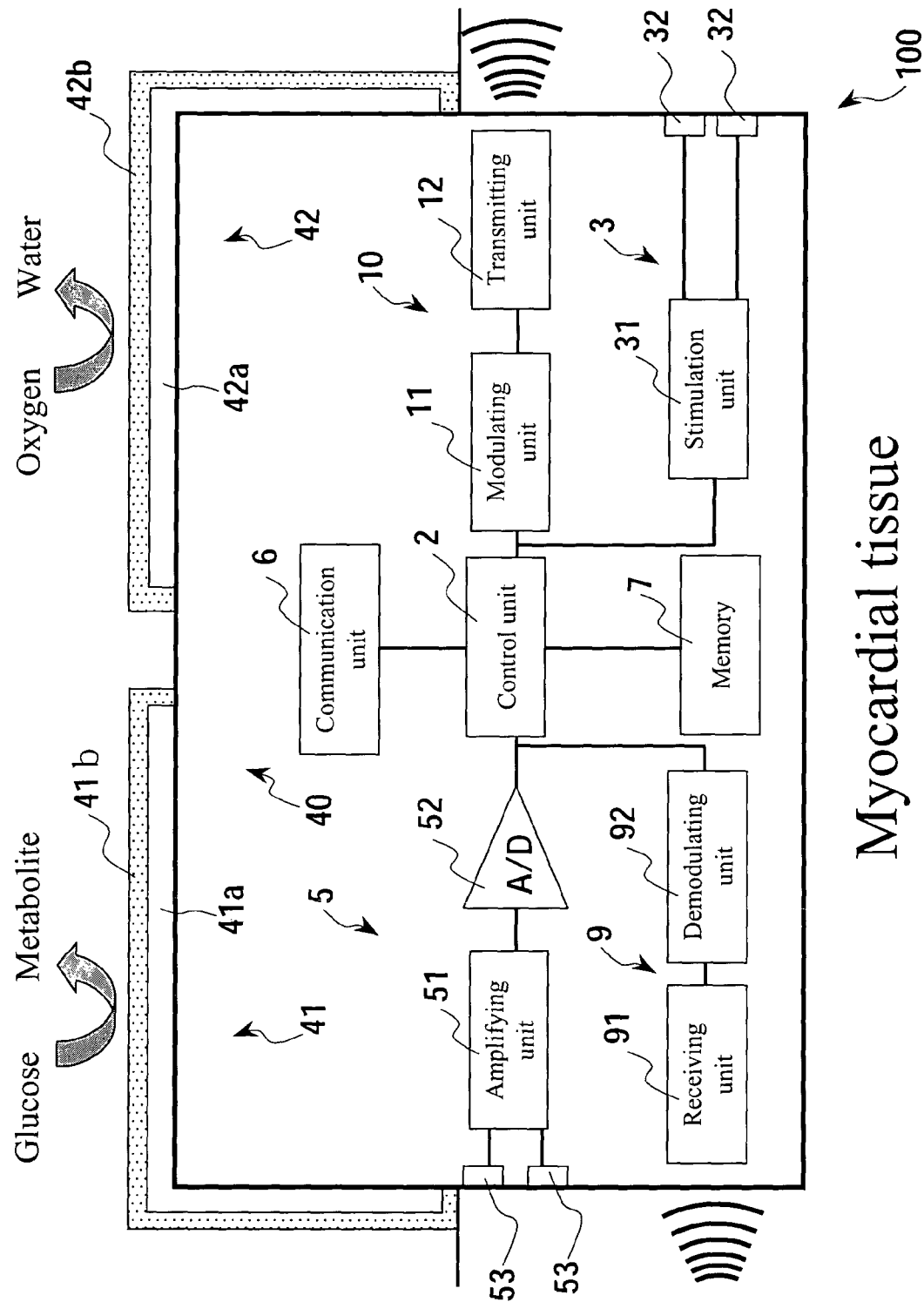
FIG. 2 is a simplified block diagram of an ultra miniature integrated cardiac pacemaker in accordance with the first embodiment.

An example of the composition of the preferable biological fuel cell (40) for this invention will be explained by referring to the diagram. FIG. 2 is a schematic diagram illustrating the simplified structure of the biological fuel cell (40) as the power unit in the ultra miniature integrated cardiac pacemaker (100) of the first embodiment.

The biological fuel cell (40) is composed of an anode (41) and a cathode (42). This biological fuel cell utilizes blood or body fluid as the electrolyte solution, and also utilizes sugars and oxygen in blood and body fluid as biological fuels. Therefore, the anode electrode (41*a*) and the cathode electrode (42*a*) are positioned so as to be in contact with blood or body fluid. In FIG. 2, the anode electrode (41*a*) and the cathode electrode (42*a*) are designed to be in contact with blood, and the heart stimulating electrode (32) and the electrocardiographic information recording electrode (53) are in contact with the myocardial tissue.

The anode (41) is composed of an anode electrode (41*a*) and an immobile layer (41*b*) coating the surface of the anode electrode (41*a*). A gold electrode, etc. is preferably used as the anode electrode (41*a*).

Oxidative enzymes of biological fuels and mediators necessary for the oxidation of biological fuels are immobilized on the surface of the anode electrode (41*a*).

Carbohydrates are used as biological fuels. Examples of carbohydrates are monosaccharides such as glucose and fructose, disaccharides such as mannitol and sucrose, and pentoses such as xylose and arabinose. Glucose, which can be supplied easily by the body, is preferably used as the fuel.

Any oxidative enzymes that oxidize biological fuels can be used in the present invention. For example, enzymes called oxidases and hydrogenases could be used. If glucose is used as the biological fuel, glucose oxidase and glucose dehydrogenase can be used. Glucose dehydrogenase is preferable.

Any mediator that can transfer electrons released from the biological fuel to the anode electrode (41*a*) can be used in the present invention. Some examples include, but are not limited to, the so-called coenzymes such as flavin adenine dinucleotide phosphate, enzymes such as laccase, quinines such as pyrrolo-quinoline quinine, and osmium complex, as well as their combinations.

The oxidative enzymes and mediators are immobilized on the surface of the anode electrode (41*a*) to form an immobile layer (41*b*). There is no restriction on the method of immobilization, and any method well known to immobilize enzymes onto an electrode surface can be used. For example, a gold disc electrode can be used as the substrate, and aminoethane-thiol is adsorbed on the surface of the gold electrode to form a monomolecular film followed by modification of the amino groups. After that, the method mixes the oxidative enzyme for biological fuel, the mediator and albumin in a beaker. Then glutaraldehyde is added to allow the enzymes and mediators to cross-link with glutaraldehyde and then the mixture is applied to the surface of the gold disc electrode.

To ensure that the reaction takes place efficiently at the anode, the immobile layer (41b) should preferably be designed such that the anode electrode (41a) does not come into contact with oxygen present in the body.

The cathode (42) is composed of a cathode electrode (42a). An example of the cathode electrode (42a) is a platinum electrode. A catalyst to enhance a reaction involving reduction of oxygen is required on the cathode electrode (42a). The platinum itself can function as the catalyst.

To ensure that the reaction takes place efficiently at the cathode, it is desirable to form a coating (42b) on the surface of the cathode electrode, which will prevent permeation of substances other than oxygen that react with the cathode electrode (42a), and at the same time allow permeation of oxygen and hydrogen ions.

The biological fuel cell (40) does not have a container filled with electrolyte solution. Instead, the cathode electrode (41a) and the anode electrode (42a) are in contact with the blood or body fluid of the body. The blood and body fluid act as the electrolyte solution. In the electrolyte solution, biological fuel and oxygen are constantly supplied by the blood flow, and at the same time metabolic products are dissolved in blood and removed by the blood flow. The supply of biological fuel and oxygen as well as the removal of metabolic products are maintained constant through the mechanism of homeostasis.

Next, the action of the biological fuel cell (40) will be discussed.

Biological fuel is dissolved in blood and body fluid and supplied to the anode (41) surface. The biological fuel supplied to the anode (41) surface is oxidized by the action of the biological fuel oxidative enzyme immobilized in the immobile layer (41b), producing carbon dioxide, hydrogen ion and intermediate metabolites, as well as electrons. Carbon dioxide, hydrogen ion and intermediate metabolites are dissolved in blood or body fluid to be excreted. Electrons are transferred to the anode electrode (41a) via mediators.

The cathode (42) surface is supplied with oxygen and hydrogen ions dissolved in blood and body fluid, and these ions react in the presence of electrons transmitted from the anode electrode (41a) to the cathode electrode (42a), and form water. This reaction generates an electric current, which is used as the driving power source.

Based on the program already saved in the memory (7) as well as on electrocardiographic information output from the electrocardiographic information detecting means (5) and information transmitted from the exterior, the control unit (2) generates control signals and outputs the signals into the heart stimulating means (3).

For instance, the control unit (2) is equipped with a stimulation timing determining means that decides the timing of stimulation to generate control signals, and a stimulation timing changing means that changes the timing of stimulation to generate control signals. Usually this unit is programmed to generate control signals at stimulation timing at a predetermined frequency. It is also programmed to change the stimulation timing when certain conditions are fulfilled; for instance, in case intracardiac P wave information is detected within a given time interval.

Furthermore, this invention can be equipped with a communication means (6). The communication means (6) communicates with an external programmer (8) installed external to the ultra miniature integrated cardiac pacemaker, and is used to change the pacing program saved in the memory (7). By this means, even after implantation of the ultra miniature integrated cardiac pacemaker in the patient, it is possible to use the external programmer (8) to change the pacing program saved in the memory (7) as appropriate for the particular patient.

For communication between the external programmer (8) and communication means (6) when a patient is implanted with multiple ultra miniature integrated cardiac pacemakers, by setting different frequencies for the individual ultra miniature integrated cardiac pacemakers, for example, it is possible to change the pacing program for each ultra miniature integrated cardiac pacemaker. Also, by conducting spread spectrum communication or by giving each pacemaker an ID, it is possible to change the pacing program of each ultra miniature integrated cardiac pacemaker.

Next, the ultra miniature integrated cardiac pacemaker of the second embodiment (110) of the present invention will be explained. The difference between the ultra miniature integrated cardiac pacemaker in the second embodiment (110) and the aforementioned ultra miniature integrated cardiac pacemaker of the first embodiment (100) is that the former has no transmitting means (10) or receiving means (9).

The ultra miniature integrated cardiac pacemaker of the second embodiment (110) can be used when there is no need to synchronize movements with other cardiac pacemakers.

Based on the control program already saved in the memory (7) and on electrocardiographic information output from the electrocardiographic information detecting means (5), the control unit (2) generates control signals and outputs the signals to the heart stimulating means (3).

Figure 3:
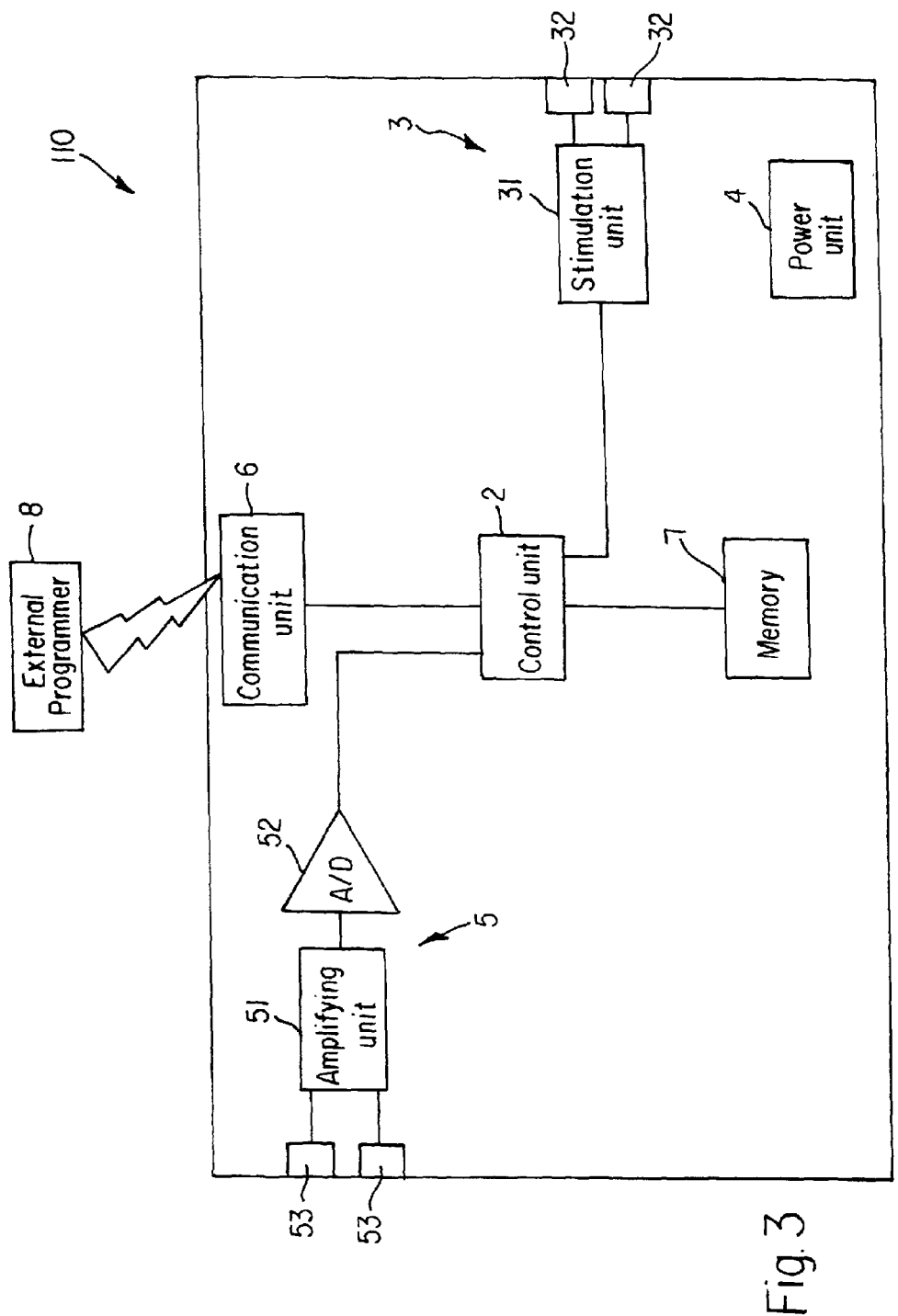
FIG. 3 is a simplified block diagram of an ultra miniature integrated cardiac pacemaker in accordance with the second embodiment.

The other components are the same as those in the aforementioned ultra miniature integrated cardiac pacemaker of the first embodiment (100), therefore explanations are omitted. In FIG. 3, the same numbers are assigned to components identical to those in the first embodiment (100) as shown in FIG. 1.

Figure 4:
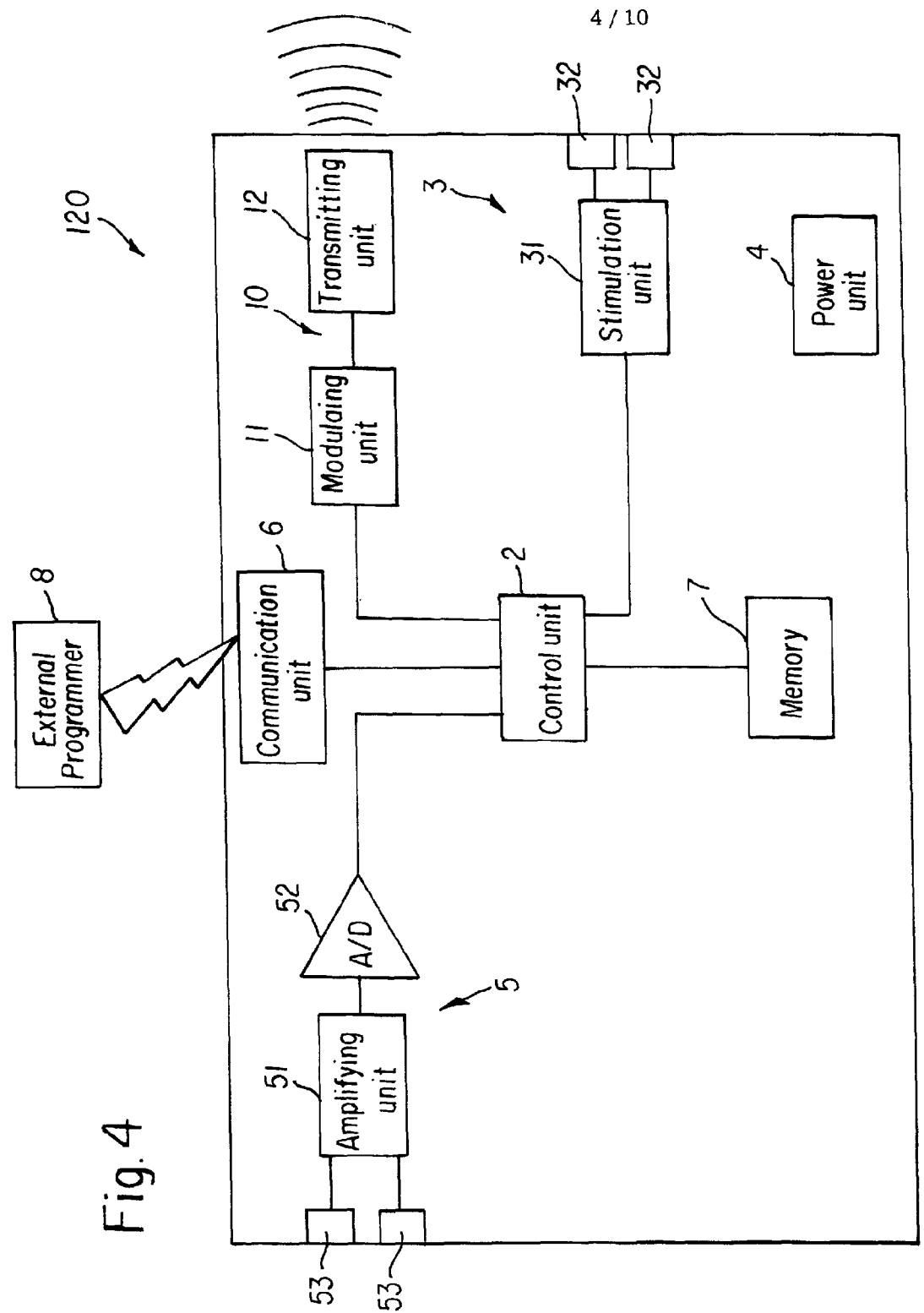
FIG. 4 is a simplified block diagram of an ultra miniature integrated cardiac pacemaker in accordance with the third embodiment.

Next, the ultra miniature integrated cardiac pacemaker of the third embodiment (120) of this invention will be explained. FIG. 4 is a simplified block diagram of the ultra miniature integrated cardiac pacemaker in this embodiment (120). The difference between the ultra miniature integrated cardiac pacemaker in this embodiment (120) and the aforementioned ultra miniature integrated cardiac pacemaker of the first embodiment is that the former has no receiving means (9).

By sending the control signals to the exterior (such as other cardiac pacemakers) via carrier waves, the ultra miniature integrated cardiac pacemaker (120) is able to synchronize and operate with, for instance, one or more other cardiac pacemakers.

Based on the control program already saved in the memory (7) and electrocardiographic information output from the electrocardiographic information detecting means (5), the control unit (2) generates control signals and outputs the signals to the heart stimulating means (3).

The other components are the same as those in the aforementioned ultra miniature integrated cardiac pacemaker of the first embodiment, therefore explanations are omitted. In FIG. 4, the same numbers are assigned to components identical to those in the ultra miniature integrated cardiac pacemaker in accordance with the first and second embodiments shown in FIGS. 1 and 3.

Next, the ultra miniature integrated cardiac pacemaker of the fourth embodiment (130) of this invention will be explained. The difference between the ultra miniature integrated cardiac pacemaker in this embodiment (130) and the aforementioned ultra miniature integrated cardiac pacemaker in the first embodiment is that the former has no transmitting means (10) to send control signals and/or electrocardiographic information to the exterior.

Through the receiving means (9) that receives information from the exterior, for example, from other cardiac pacemakers, the ultra miniature integrated cardiac pacemaker (130) is able to synchronize and operate with other cardiac pacemakers.

Based on the control program already saved in the memory (7), as well as electrocardiographic information output from the electrocardiographic information detecting means (5) and information transmitted from the exterior, the control unit (2) generates control signals and outputs the signals to the heart stimulating means (3).

Figure 5:
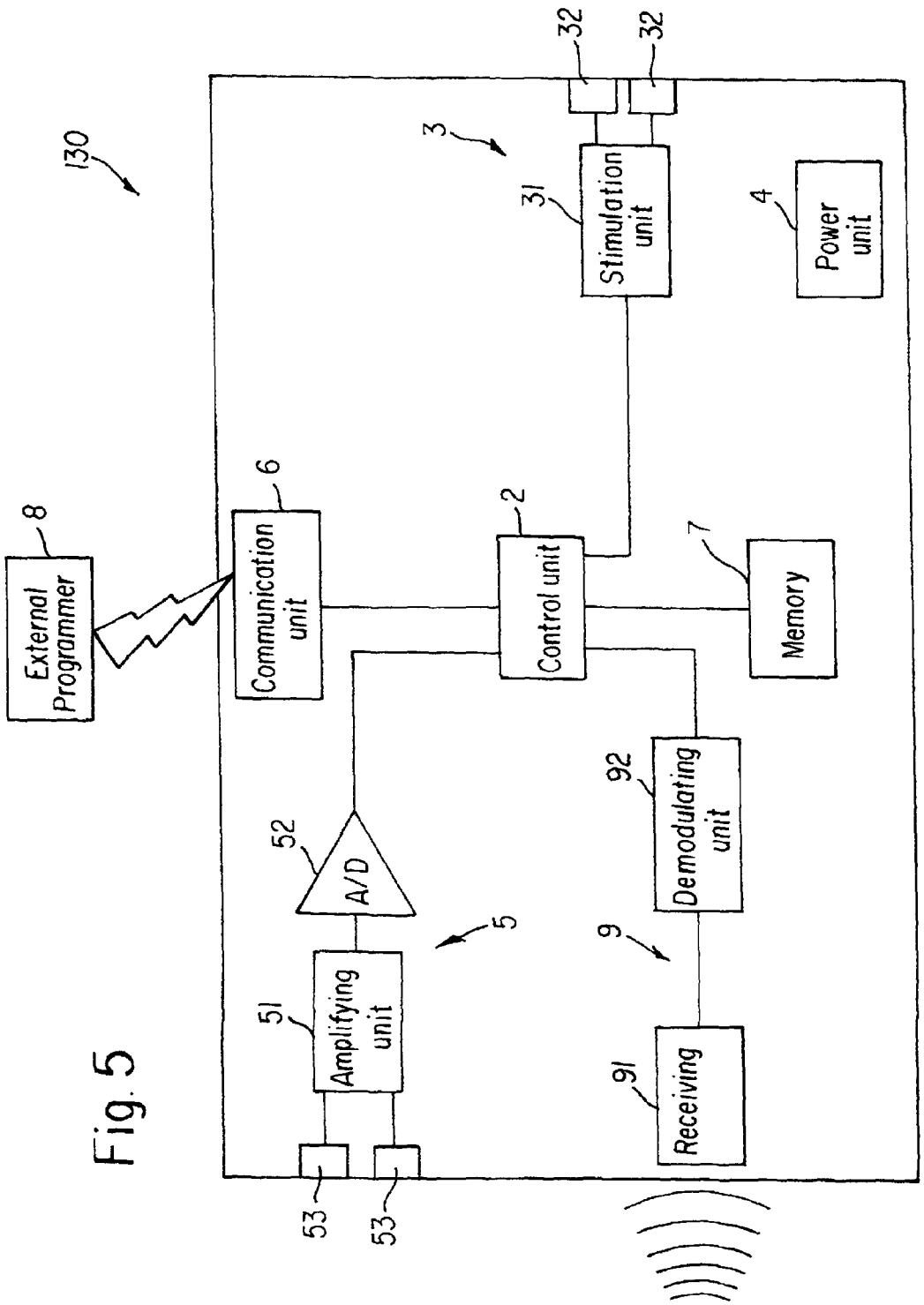
FIG. 5 is a simplified block diagram of an ultra miniature integrated cardiac pacemaker in accordance with the fourth embodiment.

The other components are the same as those in the aforementioned ultra miniature integrated cardiac pacemaker of the first embodiment, therefore explanations are omitted. In FIG. 5, the same numbers are assigned to components identical to those in the ultra miniature integrated cardiac pacemakers in accordance with the first three embodiments shown in FIGS. 1, 3 and 4.

In the ultra miniature integrated cardiac pacemakers of the first four embodiments, the electrocardiographic information recording electrodes (53) and the heart stimulating electrode (32) are shown as separate components. In reality, the electrocardiographic information recording electrode (53) and the heart stimulating electrode (32) may be shared.

Moreover, the receiving unit (91) and the transmitting unit (12) are shown as separate components; however, the receiving unit (91) and the transmitting unit (12) may also be shared.

Furthermore, by installing in the patient a sensor that measures body temperature and blood pressure and outputting the biological information obtained from these sensors to the control unit (2) of the ultra miniature integrated cardiac pacemakers of the first four embodiments, the control unit (2) is able to generate control signals based on the biological data.

In addition, for the ultra miniature integrated cardiac pacemakers of the first four embodiments, there is no particular restriction on the method of implanting the pacemaker in the heart and conventional methods for catheterization may be adopted. For instance, implantation may be done by attaching the ultra miniature integrated cardiac pacemaker to the tip of a catheter and inserting it into the predetermined position inside the heart, and then withdrawing only the catheter after fixing the pacemaker in the endocardium. In the ultra miniature integrated cardiac pacemakers of the invention, the generator main body and the electrodes are integrated, thus obviating the need for lead wires. Therefore, the ultra miniature integrated cardiac pacemakers of the invention can be made of a size of only 2 to 3 mm in diameter. There is no need to make a wide incision in the chest wall to implant the generator main body.

Next, a cardiac pacing system according to this invention using the aforementioned ultra miniature integrated cardiac pacemakers in accordance with the first four embodiments of this invention will be described while referring to the diagrams.

Figure 6:
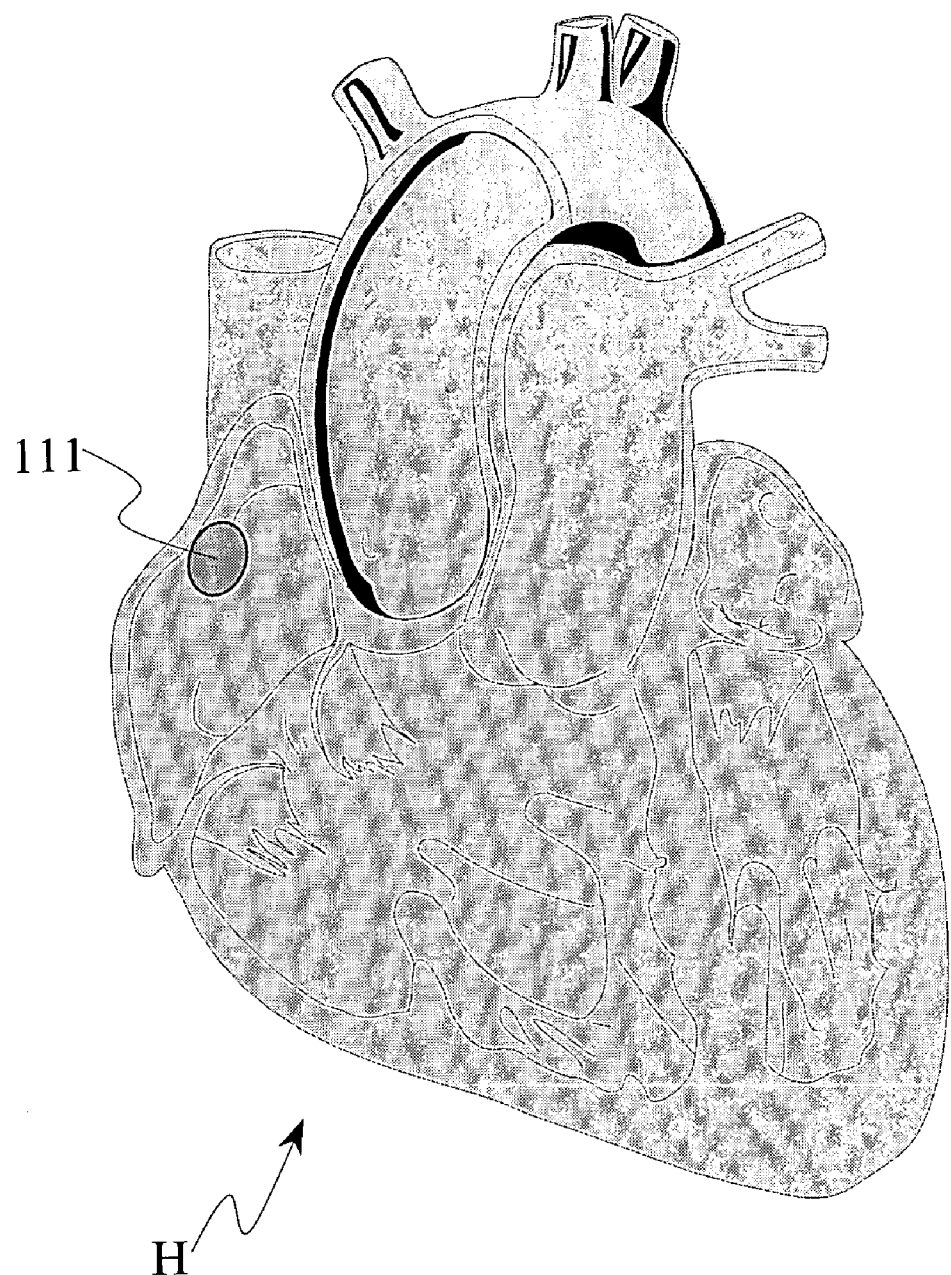
FIG. 6 is a schematic diagram illustrating a first application of the ultra miniature integrated cardiac pacemaker in accordance with the present invention (the first distributed cardiac pacing system).

FIG. 6 is a schematic diagram illustrating the outline of one embodiment of the cardiac pacing system. One ultra miniature integrated cardiac pacemaker (111) is implanted into the atrial endocardium of the patient. In FIG. 6 as well as in FIGS. 7 to 10 to be described below, H indicates the heart.

The cardiac pacing system in this embodiment is preferred in cases where the atrium has lost the ability to keep pace although the electrical activity in the atrium and the electrical activity in the ventricle remain synchronized. For example, it may be indicated for patients with sick sinus syndrome in whom only sinus node function is impaired, while intra-atrial conduction and atrio-ventricular conduction are preserved.

The ultra miniature integrated cardiac pacemaker (111) implanted in the atrium is equipped with a control unit that outputs control signals, a heart stimulating means that responds to the control signals and electrically stimulates the atrial muscle, and an electrocardiographic information detecting means that detects the electrocardiographic information including at least intracardiac P wave information. It is designed such that the detected electrocardiographic information is output into the control unit. In other words, although the ultra miniature integrated cardiac pacemaker of the second embodiment of this invention is preferably used, the ultra miniature integrated cardiac pacemaker in accordance with the first, third and fourth embodiments can also be used as long as they possess the above-mentioned designs.

Also, the control unit is equipped with a stimulation timing determining means that decides the timing of stimulation to generate control signals, and a stimulation timing changing means that changes the timing of stimulation to generate control signals.

One example of operation of the cardiac pacing system in this embodiment will be explained below. By the stimulation timing determining means, control signals are generated according to a predetermined stimulation timing and the atrial endocardium is stimulated electrically. This results in excitation and contraction of the atrial myocardium, while at the same time this stimulus is conducted to the atrioventricular node through intra-atrial conduction pathway. Then, from the atrioventricular node, the stimulus is conducted to the His bundle, the left and right bundle branch, the Purkinje fiber and finally exciting the ventricular myocardium, resulting in a normal heart beat.

Even in sick sinus syndrome, a spontaneous heart beat may occur. If the electrocardiographic information detecting means detects spontaneous intracardiac P wave information within a given predetermined time from the prior heart beat, this spontaneous intracardiac P wave information is output into the control unit, meanwhile the timing of stimulation to generate control signals is changed by the stimulation timing changing means of the control unit, and atrial pacing is suppressed. In case spontaneous intracardiac P wave information is not detected within a given time interval after the detection of prior intracardiac P wave information, the atrial myocardium will be stimulated electrically according to the predetermined stimulation timing.

By placing the above-mentioned ultra miniature integrated cardiac pacemaker in the ventricular endocardium of the patient, it is possible to stimulate the ventricular myocardium. By applying this pacemaker to patients who have normal sinus node function and only impaired atrioventricular conduction, it is possible to maintain the clinically required minimal number of ventricular contraction although there is no synchrony between the atrium and ventricle.

Next, a distributed cardiac pacing system according to another embodiment will be explained while referring to the diagrams.

Figure 7:
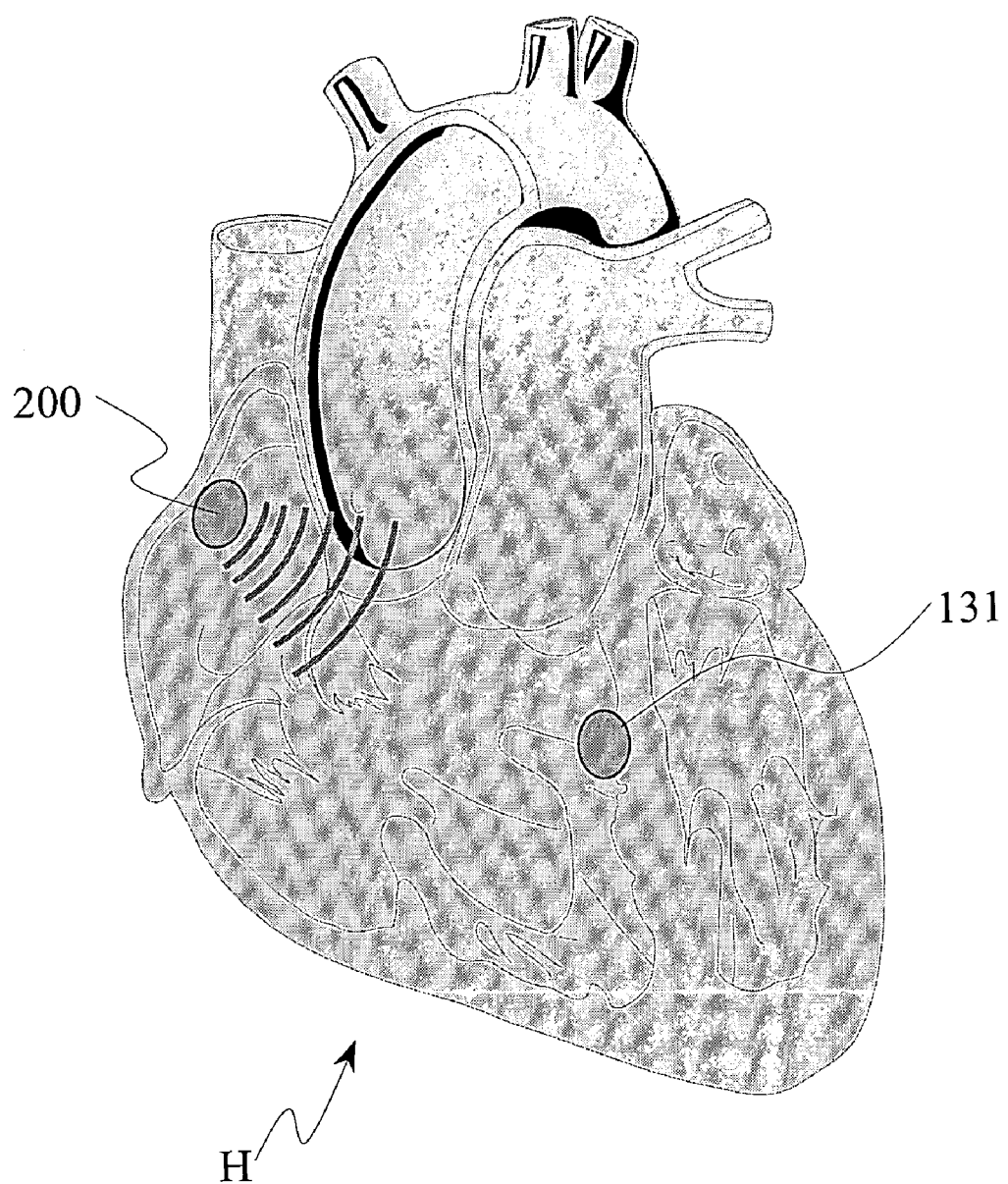
FIG. 7 is a schematic diagram illustrating a second application of the ultra miniature integrated cardiac pacemaker in accordance with the present invention (the second distributed cardiac pacing system).
Figure 8:
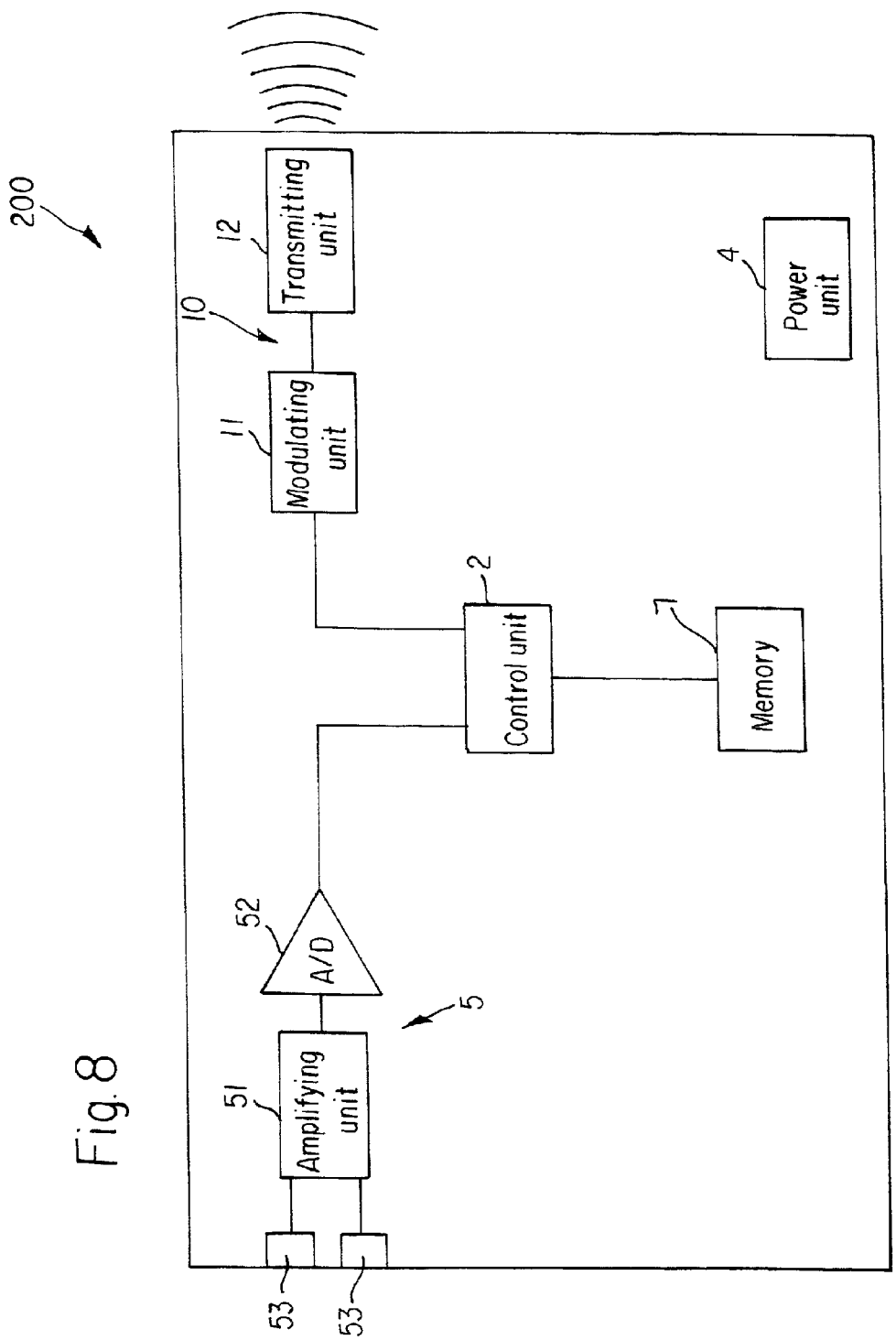
FIG. 8 is a block diagram illustrating an outline of the electrocardiographic information detection device.

FIG. 7 is a schematic diagram illustrating an outline of the distributed cardiac pacing system according to this embodiment. The schematic diagram shows one electrocardiographic information detecting device (200) in the atrial endocardium and one ultra miniature integrated cardiac pacemaker in accordance with this invention (131) in the ventricular endocardium. FIG. 8 is a block diagram illustrating the outline of the electrocardiographic information detecting device (200).

The distributed cardiac pacing system in this embodiment is indicated for patients who have normal sinus node function and whose atrioventricular conduction is only impaired. In detail, the electrocardiographic information detecting device (200) placed in the atrial endocardium detects electrocardiographic information including at least spontaneous intracardiac P wave information. The detected electrocardiographic information including spontaneous intracardiac P wave information is transmitted to the ultra miniature integrated cardiac pacemaker (131) placed in the ventricular endocardium. Upon receiving the electrocardiographic information of the spontaneous intracardiac P wave information from the electrocardiographic information detecting device (200) and after a given lag (atrioventricular delay equivalent to the PQ interval in the electrocardiogram), the ultra miniature integrated cardiac pacemaker (131) conducts ventricular pacing by electrically stimulating the ventricular myocardium by the heart stimulating means.

Even in patients with impaired atrioventricular conduction, spontaneous ventricular contraction may occur. In these patients, if ventricular contraction occurs (in case of detection of spontaneous intracardiac QRS complex information) within a given time (atrioventricular delay) after the detection of spontaneous intracardiac P wave information, the stimulation timing is changed and ventricular pacing is not conducted.

FIG. 8 is a block diagram illustrating the outline of the electrocardiographic information detection device (200) placed in the atrial endocardium. The electrocardiographic information detection device (200) is composed of an electrocardiographic information detecting means (5) that detects the electrocardiographic information including at least intracardiac P wave information and outputs the electrocardiographic data, a transmitting means that sends electrocardiographic information (10), and a control unit (2).

In the electrocardiographic information detection device (200) shown in the diagram, the electrocardiographic information detecting means (5) is composed of two electrocardiographic information recording electrodes (53) that detect electrocardiographic information, an amplifying unit (51) that amplifies the electrocardiographic information (51), and an A/D conversion unit (52) that converts the electrocardiographic information into digital information.

Moreover, in the electrocardiographic information detection device (200) shown in the diagram, the transmitting means (10) is composed of a modulating unit (11) that inputs and modulates the electrocardiographic information output from the control unit (2), and a transmitting unit (12) that sends the modulated electrocardiographic information by specified carrier wave. The modulated electrocardiographic information is sent to the ultra miniature integrated cardiac pacemaker (131) placed in the ventricular endocardium.

The ultra miniature integrated cardiac pacemaker (131) placed in the ventricle is composed of a control unit that outputs control signals, a heart stimulating means that responds to the control signal and electrically stimulates the ventricular myocardium, an electrocardiographic information detecting means that detects the electrocardiographic information including at least intracardiac QRS complexes, and a receiving means that receives and demodulates the electrocardiographic information sent from the electrocardiographic information detection device (200) placed in the atrium. It is designed such that the electrocardiographic information detected by the electrocardiographic detecting means and the electrocardiographic information sent from elsewhere is input into the control unit. Therefore, in the distributed cardiac pacing system of this embodiment, the ultra miniature integrated cardiac pacemakers of the fourth embodiment are preferably used as the ultra miniature integrated cardiac pacemakers placed in the ventricular endocardium, but the ultra miniature integrated cardiac pacemakers of the first embodiment can also be used without a problem.

Furthermore, the control unit is equipped with a stimulation timing determining means that decides the timing of stimulation to generate control signals, and a stimulation timing changing means that changes the timing of stimulation to generate control signals.

One example of operation of the distributed cardiac pacing system in this embodiment will be explained below. Usually, the ventricle is paced by the generation of control signals at a stimulation timing determined by the stimulation timing determining device [pacing after a given time interval (atrioventricular delay) from the detection of intracardiac P wave information].

If spontaneous intracardiac QRS complex information is detected within a given time interval (atrioventricular delay) after the detection of intracardiac P wave information, the timing of stimulation to generate control signals is changed by the stimulation timing changing means, and control signals are not generated.

The ultra miniature integrated cardiac pacemaker (131) is preferably designed such that the ventricle is paced at regular intervals if no intracardiac P wave information is sent from the electrocardiographic information detection device (200) within a given time interval after intracardiac QRS complex information is detected (due to spontaneous ventricular contraction or due to stimulation by a cardiac pacemaker). This design will assure safety if sinus arrest or sinoatrial block occurs.

Figure 9:
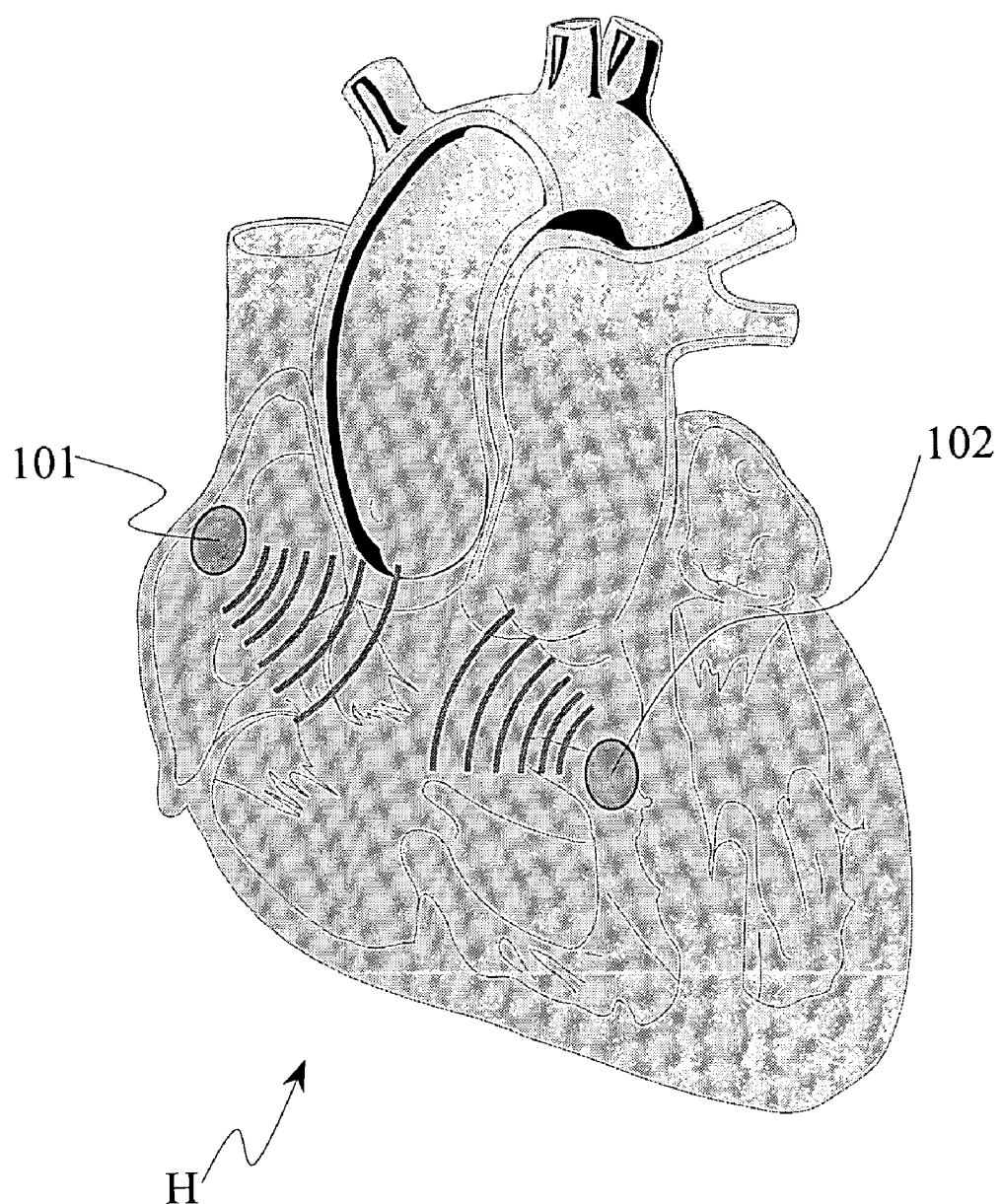
FIG. 9 is a schematic diagram illustrating a third application of the ultra miniature integrated cardiac pacemaker in accordance with the present invention (the third distributed cardiac pacing system).

Next, the distributed cardiac pacing system in another embodiment will be explained while referring to the diagram. FIG. 9 is a schematic diagram illustrating a distributed cardiac pacing system according to this embodiment. The diagram shows a first ultra miniature integrated cardiac pacemaker (101) placed in the atrial endocardium and a second ultra miniature integrated cardiac pacemaker (102) placed in the ventricular endocardium.

The distributed cardiac pacing system in this embodiment may be indicated for patients with malfunction of the sinus node together with impaired atrioventricular conduction. In other words, this pacemaker is indicated for patients with sick sinus syndrome with manifestations of both arrest of sinus function and atrioventricular block.

One example of operation of the distributed cardiac pacing system in this embodiment will be explained. The first ultra miniature integrated cardiac pacemaker (101) placed in the atrial endocardium outputs control signals and paces the atrium by the heart stimulating means. This control signal (and/or electrocardiographic information of atrium) is modulated into carrier waves and transmitted to the second ultra miniature integrated cardiac pacemaker (102) placed in the ventricular endocardium. Upon receiving the control signals (and/or electrocardiographic information of the atrium) from the first ultra miniature integrated cardiac pacemaker (101), the second ultra miniature integrated cardiac pacemaker (102) outputs control signals with a given delay (atrioventricular delay equivalent to the PQ interval on electrocardiogram) after the atrial pacing by the first ultra miniature integrated cardiac pacemaker (102), and electrically stimulates the ventricular myocardium to conduct ventricular pacing. Furthermore, this control signal (and/or electrocardiographic information of the ventricle) is modulated into a carrier wave and transmitted to the first ultra miniature integrated cardiac pacemaker (101). The first ultra miniature integrated cardiac pacemaker (101) suppresses detection of intracardiac P wave for a given time interval after receiving the control signal (and/or electrocardiographic information of the ventricle) from the second ultra miniature integrated cardiac pacemaker (102). Thereafter, the first ultra miniature integrated cardiac pacemaker (101) outputs control signals at a stimulation timing according to a predetermined rate, and stimulates the atrium.

By repeating the above, it is possible to pace the heart and mimic the natural physiological state.

Even patients with sick sinus syndrome with manifestations of both arrest of sinus function and atrioventricular block may generate spontaneous ventricular contraction or atrial contraction. If spontaneous intracardiac P wave information is detected within a given time from the prior heart beat, then the atrial pacing is suppressed. Moreover, if spontaneous intracardiac QRS complex information is detected within a given time interval (atrioventricular delay) after the detection of intracardiac P wave information (spontaneous or due to the first ultra miniature integrated cardiac pacemaker), then ventricular pacing is suppressed.

The first ultra miniature integrated cardiac pacemaker (101) placed in the atrial endocardium is equipped with a control unit that outputs control signals, a heart stimulating means that responds to the control signal and electrically stimulates the atrial myocardium, an electrocardiographic information detecting means that detects the electrocardiographic information including at least intracardiac P wave information, a transmitting means that modulates the control signal or electrocardiographic information and sends the information to the second ultra miniature integrated cardiac pacemaker (102) placed in the ventricle, and a receiving means that receives and demodulates the control signal or electrocardiographic information sent from the second ultra miniature integrated cardiac pacemaker (102) placed in the ventricle. The pacemaker is designed such that the control signal and electrocardiographic information sent from the second ultra miniature integrated cardiac pacemaker (102) are input into the control unit. Therefore, in the distributed cardiac pacing system of this embodiment (101), the ultra miniature integrated cardiac pacemaker of the first embodiment is preferably used as the first ultra miniature integrated cardiac pacemaker (101).

The second ultra miniature integrated cardiac pacemaker (102) is equipped with a control unit that outputs control signals, a heart stimulating means that responds to the control signal and electrically stimulates the ventricular myocardium, an electrocardiographic information detecting means that detects the electrocardiographic information including at least intracardiac QRS complex information, a transmitting means that modulates the control signal or electrocardiographic information and sends the information to the first ultra miniature integrated cardiac pacemaker (101), and a receiving means that receives and demodulates the control signal or electrocardiographic information sent by the first ultra miniature integrated cardiac pacemaker (101) placed in the atrium. The pacemaker is designed such that the control signal and electrocardiographic information sent from the first ultra miniature integrated cardiac pacemaker (101) are input into the control unit. Therefore, in the distributed cardiac pacing system of this embodiment, the abovementioned ultra miniature integrated cardiac pacemaker of the first embodiment is preferably used as the second ultra miniature integrated cardiac pacemaker (102).

In the first ultra miniature integrated cardiac pacemaker (101), the control unit is equipped with a stimulation timing determining means that decides the timing of stimulation to generate control signals, and a stimulation timing changing means that changes the timing of stimulation to generate control signals.

Usually, the stimulation timing determining means decides the timing of stimulation of control signal generation, and then generates control signals to conduct atrial pacing.

One example of operation of the first ultra miniature integrated cardiac pacemaker (101) will be explained. If the electrocardiographic information detecting means detects spontaneous intracardiac P wave within a given time from the prior heart beat, the timing of stimulation to generate control signals is changed, a control signal is not generated and atrial pacing is not conducted. If the electrocardiographic information detecting means does not detect spontaneous intracardiac P wave information within a given time interval from the last heart beat, then a control signal is generated and atrial pacing is conducted.

Moreover, in the control unit, if the control signal is generated or spontaneous intracardiac P wave information is detected, the information is sent from the transmitting unit to the second ultra miniature integrated cardiac pacemaker (102).

In the second ultra miniature integrated cardiac pacemaker (102), the control unit is equipped with a stimulation timing determining means that decides the timing of stimulation to generate control signals, and a stimulation timing changing means that changes the timing of stimulation to generate control signals.

One example of operation of the second ultra miniature integrated cardiac pacemaker (102) will be explained. Usually, a control signal is generated at a timing predetermined by the timing determining means [the control signal is generated at a given time interval (atrioventricular delay) after the control signal or intracardiac P wave information is sent from the first ultra miniature integrated cardiac pacemaker (101)].

If spontaneous intracardiac QRS complex information is detected within a given time (atrioventricular delay), the timing of stimulation to generate control signals is changed by the stimulation timing changing means and ventricular pacing is not conducted.

Moreover, in the control unit, if a control signal is generated or spontaneous intracardiac QRS wave information is detected, the information is sent from the transmitting unit to the first ultra miniature integrated cardiac pacemaker (101). The first ultra miniature integrated cardiac pacemaker (101) suppresses the detection of intracardiac P wave information for a given time interval after receiving the control signal (or electrocardiographic information of the ventricle) from the second ultra miniature integrated cardiac pacemaker (102). This design is essential to prevent the complication of so called pacemaker tachycardia caused by the following mechanism: when intracardiac QRS complex due to spontaneous ventricular contraction is conducted retrograde to the atrium, the first ultra miniature integrated cardiac pacemaker detects intracardiac P wave information, based on which the second ultra miniature integrated cardiac pacemaker electrically stimulates the ventricle, resulting in repeated electrical stimulation of the ventricle.

Figure 10:
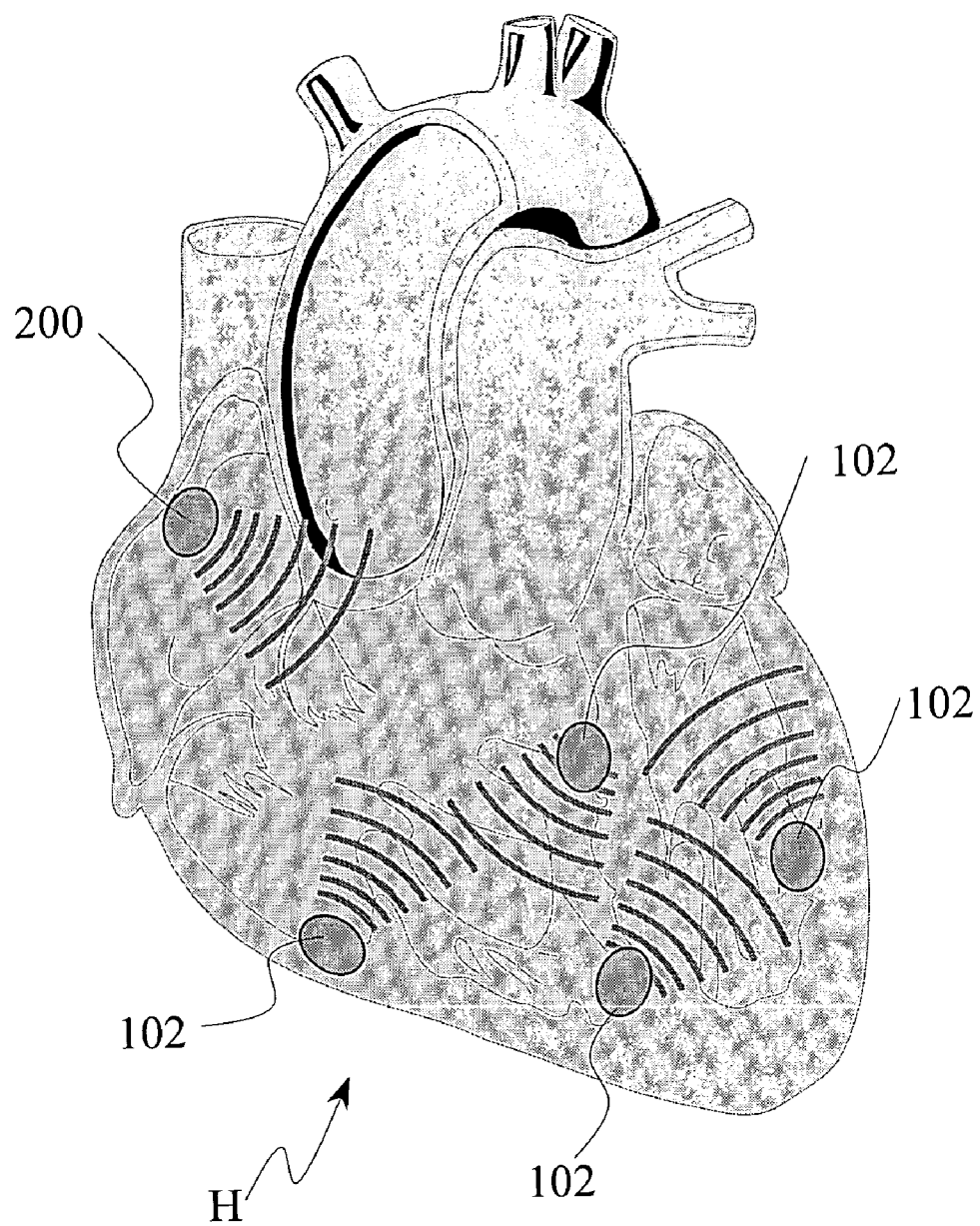
FIG. 10 is a schematic diagram illustrating a fourth application of the ultra miniature integrated cardiac pacemaker in accordance with the present invention (the fourth distributed cardiac pacing system).

Next, a distributed cardiac pacing system in another embodiment will be explained while referring to the diagram. FIG. 10 is a schematic diagram illustrating the distributed cardiac pacing system in this embodiment. The diagram shows an electrocardiographic information detecting device (200) placed in the atrial endocardium and multiple (for example, a total of 4 in FIG. 10) ultra miniature integrated cardiac pacemakers (102) placed in the ventricular endocardium.

The distributed cardiac pacing system in this embodiment may be indicated for patients with impaired synchrony of ventricular myocardial contraction leading to lowered ventricular contractility, or patients at risk for fatal arrhythmia.

One example of operation of this distributed cardiac pacing system will be explained. The electrocardiographic information detecting device (200) placed in the atrial endocardium detects electrocardiographic information including at least intracardiac P wave information. The detected electrocardiographic information is sent to multiple ultra miniature integrated cardiac pacemakers (102) placed in the ventricular endocardium. Once electrocardiographic information is sent from the electrocardiographic information detecting device (200), multiple ultra miniature integrated cardiac pacemakers (102) generate control signals to stimulate the ventricular myocardium and pace the ventricle with a delay after atrial contraction in time lags that vary depending on the individual ultra miniature integrated cardiac pacemakers (102). In other words, once electrocardiographic information is sent from the electrocardiographic information detecting device (200), the multiple ultra miniature integrated cardiac pacemakers (102) pace the ventricle after predetermined times depending on the ventricular sites at which the individual ultra miniature integrated cardiac pacemakers (102) are placed.

If spontaneous ventricular contraction occurs, that is, if spontaneous intracardiac QRS complex information is detected within a given time interval (atrioventricular delay) after the detection of intracardiac P wave information, ventricular pacing is suppressed. However, even though spontaneous intracardiac QRS complex information is detected, if the spontaneous beat is not detected within given time intervals at other multiple ultra miniature integrated cardiac pacemakers (102) placed in the ventricular endocardium, the ventricular pacing at these sites will not be suppressed. In order to realize this, spontaneous intracardiac QRS complex information recorded by a pacemaker (102) at any site of the ventricle is transmitted to other ventricular pacemakers (102). Each ventricular pacemaker (102) mutually receives the signals sent from other ventricular pacemakers (102).

The ultra miniature integrated cardiac pacemaker (102) placed in the ventricular endocardium is equipped with a control unit that outputs control signals, a heart stimulating means that responds to control signals and electrically stimulates the ventricular myocardium, an electrocardiographic information detecting means that detects the electrocardiographic information including at least intracardiac QRS complex information, a transmitting means that modulates the control signal or electrocardiographic information and sends the information to other ultra miniature cardiac pacemakers placed in the ventricle, and a receiving means that receives and demodulates control signals or electrocardiographic information sent by the electrocardiographic information detecting device (200) placed in the atrium and other ultra miniature integrated cardiac pacemakers placed in the ventricle. Therefore, in this embodiment, the aforementioned ultra miniature integrated cardiac pacemakers of the first embodiment (100) are preferably used as the ultra miniature integrated cardiac pacemakers (102).

In addition, the sites where the ultra miniature integrated cardiac pacemakers are to be placed and the number of the pacemakers will be set appropriately in accordance with the patient's symptoms.

The control unit of each ultra miniature integrated cardiac pacemaker (102) is equipped with a stimulation timing determining means that decides the timing of stimulation to generate control signals, and a stimulation timing changing means that changes the timing of stimulation to generate control signals.

One example of operation of the ultra miniature integrated cardiac pacemaker will be explained. The stimulation timing determining means generates a control signal at a predetermined stimulation timing [generates a control signal at a given time interval (atrioventricular delay) after spontaneous intracardiac P wave information is transmitted from the electrocardiographic information detecting device (200)], and ventricular pacing is conducted.

The stimulation timing is different for each of the ultra miniature integrated cardiac pacemakers; in other words, it differs depending on the placement site of the pacemakers in the ventricular endocardium. For example, each ultra miniature integrated cardiac pacemaker (102) is stimulated with a time lag depending on when the site is stimulated in the normal ventricular beat. But, the above-mentioned combination is not restricted as long as it is a combination that maximally improves the contractility of the heart.

This kind of synchronized cardiac contraction also reduces the electrical instability of the ventricle, and is used to prevent arrhythmia in patients with a risk of fatal arrhythmia, and also to prevent pacemaker-induced arrhythmia.

The intracardiac QRS complex information detected by the ultra miniature integrated cardiac pacemaker (102) is transmitted to other ultra miniature integrated cardiac pacemakers via the transmitting means. If a certain ventricular pacemaker detects spontaneous intracardiac QRS complex within the predetermined time but this spontaneous beat is not detected at other ventricular pacemakers within given times, the above-mentioned design ensures that ventricular pacing also takes place in these sites.

In the distributed cardiac pacing system, it is possible to place an ultra miniature integrated cardiac pacemaker (101), instead of the electrocardiographic information detecting device (200), in the atrial endocardium just like the above-mentioned distributed cardiac pacing system in the previous embodiment. As described in the distributed cardiac pacing system in the previous embodiment (i.e., the third embodiment of the distributed cardiac pacing system), the ultra miniature integrated cardiac pacemaker placed in the atrial endocardium is equipped with a stimulation timing determining means and stimulation timing changing means, and therefore may be used in patients with lowered ventricular contractility accompanying sinus arrest and atrioventricular block, as well as in patients with a risk of fatal arrhythmia accompanying sinus arrest and atrioventricular block.

In the distributed cardiac pacing system of this revised embodiment, for the design of the ultra miniature integrated cardiac pacemaker placed in the atrial endocardium, one may adopt the design of the ultra miniature integrated cardiac pacemaker (101) placed in the atrial endocardium in the above-mentioned distributed cardiac pacing system in accordance with the previous embodiment (i.e., the third embodiment of the distributed cardiac pacing system). Furthermore, in the distributed cardiac pacing system in accordance with this revised embodiment for the design of the ultra miniature integrated cardiac pacemaker placed in the ventricular endocardium, one may adopt the design of the ultra miniature integrated cardiac pacemaker (102) placed in the ventricular endocardium in the above-mentioned distributed cardiac pacing system in this embodiment (i.e., the fourth embodiment of the distributed cardiac pacing system).

The ultra miniature integrated cardiac pacemaker in one embodiment transmits control signals or electrocardiographic information to other ultra miniature integrated cardiac pacemakers and at the same time receives control signals or electrocardiographic information from other ultra miniature integrated cardiac pacemakers; thus it is able to pace the heart in synchrony with other ultra miniature integrated cardiac pacemakers.

The ultra miniature integrated cardiac pacemaker in another embodiment does not require lead wires to connect the pacemaker main body with the stimulation electrodes; thus it is able to pace the heart without imposing extra burden on the patient.

The ultra miniature integrated cardiac pacemaker in another embodiment transmits control signals or electrocardiographic information to other ultra miniature integrated cardiac pacemakers; thus it is able to pace the heart in synchrony with other ultra miniature integrated cardiac pacemakers.

The ultra miniature integrated cardiac pacemaker in yet another embodiment receives control signals or electrocardiographic information from other ultra miniature integrated cardiac pacemakers; thus it is able to pace the heart in synchrony with other ultra miniature integrated cardiac pacemakers.

The distributed cardiac pacemaker system in another embodiment can be used for pacing in patients whose atrium has lost the ability to keep pace although the electrical activity in the atrium and the electrical activity in the ventricle remain synchronized.

The distributed cardiac pacemaker system in still another embodiment can be used in patients with normal sinus node function but in whom atrioventricular conduction is only impaired.

The distributed cardiac pacemaker system in another embodiment can be used in patients whose sinus node is not functioning normally and atrioventricular conduction is also impaired.

The distributed cardiac pacemaker system in yet another embodiment can be used in patients who have lost synchrony of contraction among various parts of the ventricle together with lowered ventricular contractility, or patients with arrhythmia.

The distributed cardiac pacemaker system in another embodiment can be used in patients with lowered ventricular contractility accompanying sinus arrest and atrioventricular block, as well as patients with a risk of fatal arrhythmia accompanying sinus arrest and atrioventricular block.

The present invention provides an ultra miniature integrated cardiac pacemaker and distributed cardiac pacing system which allow pacing of the heart without the need for the conventional lead wires that connect the electrodes with the pacemaker main body, and allow implantation in the heart by catheter manipulation only without incision of the chest wall to reduce burden on the patient.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

The invention claimed is:

1. A first ultra miniature integrated cardiac pacemaker adapted to be part of a distributed cardiac pacing system comprising at least one second ultra miniature integrated cardiac pacemaker, wherein the first ultra miniature integrated cardiac pacemaker is adapted to be implanted into a heart of a patient, the first ultra miniature integrated cardiac pacemaker comprising:
   a) a control unit that outputs at least one control signal;
   b) a heart stimulating means that responds to the control signal and electrically stimulates heart tissue;
   c) an electrocardiographic information detecting means that detects a plurality of electrocardiographic information and outputs the electrocardiographic information to the control unit;
   d) a transmitting means to modulate the electrocardiographic information and control signal and to send the modulated electrocardiographic information and the modulated control signal outside of the first ultra miniature integrated cardiac pacemaker via a plurality of carrier waves to at least one of the second ultra miniature integrated cardiac pacemakers adapted to be implanted into the heart of the patient;
   e) a receiving means to demodulate information transmitted from at least one of the second ultra miniature integrated cardiac pacemakers adapted to be implanted into the heart; and
   f) a power unit that supplies the driving power;
   wherein the first ultra miniature integrated cardiac pacemaker requires no chest incision, and can be implanted into a heart by attaching the first ultra miniature integrated cardiac pacemaker to a tip of a catheter and extracting the catheter after implantation;
   wherein the first ultra miniature integrated cardiac pacemaker is designed such that information sent from at least one of the second ultra miniature integrated cardiac pacemakers is input into the control unit after the information is demodulated by the receiving means;
   wherein the control unit of the first ultra miniature integrated cardiac pacemaker outputs the control signal based on information selected from the group consisting of a) information sent from at least one of the second ultra miniature integrated cardiac pacemakers; b) electrocardiographic information; and c) a combination of a) and b);
   wherein the control unit of the first ultra miniature integrated cardiac pacemaker outputs the control signal based on the information sent from at least one of the second ultra miniature integrated cardiac pacemakers to pace the heart and mimic a natural physiological state of the heart;
   wherein the control unit includes a stimulation timing determining means that determines the timing of stimulation to generate control signals, and a stimulation timing changing means that changes the timing of stimulation to generate control signals;
   wherein the control unit changes the stimulation timing when certain conditions are fulfilled;
   wherein the power unit is a biological fuel cell that extracts electrons from oxidative reactions of biological fuels;
   wherein the biological fuel cell is composed of an anode and a cathode;
   wherein the anode comprises an anode electrode and an immobile layer formed on a surface of the anode electrode by immobilization of mediators and oxidative enzymes for biological fuels, wherein said immobile layer prevents oxygen existing in a biological body from contacting said anode electrode;
   wherein the cathode comprises a cathode electrode and a coating material formed on a surface of the cathode electrode, wherein the cathode electrode is composed of a catalyst to enhance a reaction involving reduction of oxygen, and wherein said coating material is capable of preventing permeation of reactive substances other than oxygen and allowing permeation of oxygen and hydrogen ions;

wherein the biological fuel cell uses an electrolyte solution selected from the group consisting of blood; body fluid; and blood and body fluid, and utilizes biological fuels and oxygen in the electrolyte solution without the need for a container to contain the electrolyte solution or a metabolic product; and wherein said anode and said cathode are adapted to contact the electrolyte solution.

2. The ultra miniature integrated cardiac pacemaker of claim 1, wherein the first ultra miniature integrated cardiac pacemaker is adapted to be placed on an atrium or a ventricle of the heart of the patient.

3. A distributed cardiac pacing system comprising the ultra miniature integrated cardiac pacemaker of claim 1 and at least one second ultra miniature integrated cardiac pacemaker adapted to be placed on an atrium or a ventricle of the heart of the patient.

4. A first ultra miniature integrated cardiac pacemaker adapted to be part of a distributed cardiac pacing system comprising at least one second ultra miniature integrated cardiac pacemaker, wherein the first ultra miniature integrated cardiac pacemaker is adapted to be implanted into a heart of a patient, the first ultra miniature integrated cardiac pacemaker comprising:

a) a control unit that outputs at least one control signal;
  b) a heart stimulating means that responds to the control signal and electrically stimulates heart tissue;
  c) an electrocardiographic information detecting means that detects a plurality of electrocardiographic information and outputs the electrocardiographic information to the control unit;
  d) a transmitting means to modulate the electrocardiographic information and control signal and to send the modulated electrocardiographic information and the modulated control signal via a plurality of carrier waves to at least one of the second ultra miniature integrated cardiac pacemakers adapted to be implanted into the heart of the patient;
  e) a receiving means to demodulate information transmitted from at least one of the second ultra miniature integrated cardiac pacemakers; and
  f) a power unit that supplies the driving power;

wherein the first ultra miniature integrated cardiac pacemaker requires no chest incision, and can be implanted into a heart by attaching the first ultra miniature integrated cardiac pacemaker to a tip of a catheter and extracting the catheter after implantation;

wherein the first ultra miniature integrated cardiac pacemaker is designed such that the information sent from at least one of the second ultra miniature integrated cardiac pacemakers is input into the control unit after the information is demodulated by the receiving means;

wherein the control unit of the first ultra miniature integrated cardiac pacemaker outputs the control signal based on the information sent from at least one of the second ultra miniature integrated cardiac pacemakers adapted to be implanted into the heart to pace the heart and mimic a natural physiological state of the heart;

wherein the control unit includes a stimulation timing determining means that determines the timing of stimulation to generate control signals, and a stimulation timing changing means that changes the timing of stimulation to generate control signals;

wherein the control unit changes the stimulation timing when certain conditions are fulfilled;

wherein the power unit is a biological fuel cell that extracts electrons from oxidative reactions of biological fuels;

wherein the biological fuel cell is composed of an anode and a cathode;

wherein the anode comprises an anode electrode and an immobile layer formed on a surface of the anode electrode by immobilization of mediators and oxidative enzymes for biological fuels, wherein said immobile layer prevents oxygen existing in a biological body from contacting said anode electrode;

wherein the cathode comprises a cathode electrode and a coating material formed on a surface of the cathode electrode, wherein the cathode electrode is composed of a catalyst to enhance a reaction involving reduction of oxygen, and wherein said coating material is capable of preventing permeation of reactive substances other than oxygen and allowing permeation of oxygen and hydrogen ions;

wherein the biological fuel cell uses an electrolyte solution selected from the group consisting of blood; body fluid; and blood and body fluid, and utilizes biological fuels and oxygen in the electrolyte solution without the need for a container to contain the electrolyte solution or a metabolic product; and wherein said anode and said cathode are adapted to contact the electrolyte solution.

5. The pacemaker of claim 4, wherein the control unit outputs the control signal based on additional information comprising electrocardiographic information.

6. The ultra miniature integrated cardiac pacemaker of claim 4, wherein the first ultra miniature integrated cardiac pacemaker is adapted to be placed on an atrium or a ventricle of the heart of the patient.

7. A distributed cardiac pacing system comprising the ultra miniature integrated cardiac pacemaker of claim 4 and at least one second ultra miniature integrated cardiac pacemaker adapted to be placed on an atrium or a ventricle of the heart of the patient.

* * * * *